United States Patent
Schlosberg et al.

(10) Patent No.: US 6,177,387 B1
(45) Date of Patent: Jan. 23, 2001

(54) REDUCED ODOR AND HIGH STABILITY AIRCRAFT TURBINE OIL BASE STOCK

(75) Inventors: Richard Henry Schlosberg, Bridgewater, NJ (US); Carolyn Boggus Duncan; David Wayne Turner, both of Baton Rouge, LA (US); Thomas Lee Ashcraft, Jr., Leander; William Joseph Munley, Jr., Houston, both of TX (US)

(73) Assignee: Exxon Chemical Patents Inc, Houston, TX (US)

( * ) Notice: Under 35 U.S.C. 154(b), the term of this patent shall be extended for 0 days.

(21) Appl. No.: 09/242,613

(22) PCT Filed: Aug. 30, 1996

(86) PCT No.: PCT/US96/13856
 § 371 Date: Feb. 19, 1999
 § 102(e) Date: Feb. 19, 1999

(87) PCT Pub. No.: WO98/08801
 PCT Pub. Date: Mar. 5, 1998

(51) Int. Cl.⁷ .................................................. C10M 105/38
(52) U.S. Cl. ............................................................ 508/485
(58) Field of Search ............................................. 508/485

(56) References Cited

U.S. PATENT DOCUMENTS

| | | | |
|---|---|---|---|
| 3,056,818 | 10/1962 | Werber | 260/410.6 |
| 4,124,513 | 11/1978 | Yaffe | 252/46.7 |
| 4,141,845 | 2/1979 | Yaffe | 252/46.7 |
| 4,175,045 | * 11/1979 | Timony | 252/56 |
| 4,826,633 | 5/1989 | Carr et al. | 252/56 |
| 5,324,853 | 6/1994 | Jones et al. | 560/98 |
| 5,503,761 | 4/1996 | Ashcraft, Jr. et al. | 252/56 |
| 5,698,502 | * 12/1997 | Pafford et al. | 508/485 |
| 5,817,607 | * 10/1998 | Duncan et al. | 508/485 |
| 5,830,833 | * 11/1998 | Grasshoff et al. | 508/485 |
| 5,833,876 | * 11/1998 | Schnur et al. | 252/68 |
| 5,906,769 | * 5/1999 | Schnur et al. | 252/68 |
| 5,942,474 | * 8/1999 | Tiffany et al. | 508/485 |

FOREIGN PATENT DOCUMENTS

| | | | |
|---|---|---|---|
| 0 435 253 A1 | * | 7/1991 | (EP) . |
| 0 518 567 A1 | * | 12/1992 | (EP) . |
| 0 568 349 A1 | * | 11/1993 | (EP) . |
| 0 653 479 A1 | * | 5/1995 | (EP) . |
| 0 695 797 A2 | * | 2/1996 | (EP) . |
| 93/24585 | * | 12/1993 | (WO) . |
| 98/08801 | * | 3/1998 | (WO) . |

OTHER PUBLICATIONS

PCT/US96/13856, International Search Report and Preliminary Examination Report, May, 1997.*

* cited by examiner

*Primary Examiner*—Ellen M. McAvoy
(74) *Attorney, Agent, or Firm*—Blossom E. Loo; John F. Hunt

(57) ABSTRACT

A synthetic ester composition exhibiting low odor, and high thermal and oxidative stability which comprises the reaction product of: (a) a polyol which comprises at least dipentaerythritol, e.g., technical grade pentaerythritol and mixtures of technical grade pentaerythritol or dipentaerythritol and monopentaerythritol; and (b) a mixture of monocarboxylic acids comprising at least one linear acid selected from the group consisting of between $C_5$–$C_{10}$ acids and at least one branched acid selected from the group consisting of $C_7$–$C_9$ acids, wherein the amount of $C_5$ and $C_6$ acids is between about 20 to 45 weight %, based upon the total amount of said mixture of monocarboxylic acids, and wherein said synthetic ester composition has a viscosity of at least 4 cSt at 99° C., a viscosity of less than about 8,000 cSt at 40° C., and a pour point of at least as low as −54° C.

30 Claims, No Drawings

REDUCED ODOR AND HIGH STABILITY AIRCRAFT TURBINE OIL BASE STOCK

FIELD OF THE INVENTION

The present invention generally relates to a high thermal and oxidative stability ester base stock for use in aircraft turbine oils and the like, wherein the incorporation of odorous $C_5$ acids is substantially reduced versus conventional polyol ester base stocks, while the base stock of the present invention is still capable of meeting the viscometric and low temperature properties required under Military Specification 23699C or 23699D, i.e., a lubricant having a viscosity at 210° F. (99° C.) of a least about 5.0 centistokes, a viscosity at −40° F. (−40° C.) of less than 13,000 centistokes, and a pour point of at least as low as about −65° F. (−54° C.). The synthetic ester composition can also be a complex alcohol ester or a blend of esters, so long as the complex alcohol ester or blend of esters have a total linear and branched $C_5$ acid concentration of 45 wt. % or less, based on the total acid concentration in the base stock.

BACKGROUND OF THE INVENTION

Lubricants in commercial use today are prepared from a variety of natural and synthetic base stocks admixed with various additive packages and solvents depending upon their intended application. The base stocks typically include mineral oils, highly refined mineral oils, poly alpha olefins (PAO), polyalkylene glycols (PAG), phosphate esters, silicone esters, diesters and polyol esters.

Stability requirements and the accompanying need for lubricating oils with greater stability have been increasing. As engines become smaller and tighter, and engine operating temperatures go higher, the need for higher stability lubricants has increased. In addition, higher stability lubricants which retain this feature are also desired when longer drain intervals and decreased maintenance are desired, both of which result in savings.

In end uses where higher stability is desired or required, polyol esters have been commonly used due to their high thermal and oxidative stability. One of the most demanding lubricant applications in terms of thermal and oxidative requirements is oils for aircraft turbines. In aircraft turbines, where operating temperatures and exposure to oxygen are both high, it has been the industry's practice to use polyol esters.

Most lubricating oil formulations require the addition of antioxidants (also known as oxidation inhibitors). Antioxidants retard the rate at which ester base stocks (or any base stocks) deteriorate in service, which deterioration can be evidenced by the products of oxidation such as sludge and varnish-like deposits on the metal surfaces, and by viscosity and acidity growth. Such antioxidants include arylamines (e.g., dioctyl phenylamine and phenyl alphanaphthylamine), phosphosulfurized or sulfurized hydrocarbons, and hindered phenols (e.g., butylated hydroxy toluene) and the like.

Frequently replacing the lubricating oil or adding an antioxidant to suppress oxidation increases the total cost of maintaining an engine or other mechanical device. It would be most desirable to have an ester base stock which exhibits substantially enhanced thermal/oxidative stability compared to conventional ester base stocks, thus requiring less frequent replacement due to decomposition (i.e., oxidation degradation).

High Pressure Differential Scanning Calorimetry (HPDSC) has been used to evaluate the thermal/oxidative stabilities of formulated automotive lubricating oils (see J. A. Walker, W. Tsang, SAE 801383), of synthetic lubricating oils (see M. Wakakura, T. Sato, Journal of Japanese Petroleum Institute, 24 (6), pp. 383–392 (1981)) and of polyol ester derived lubricating oils (see A. Zeeman, Thermochim, Acta, 80(1984)1). In these evaluations, the time for the bulk oil to oxidize under a fixed temperature and atmosphere, which is the induction time, was measured. Longer induction times have been shown to correspond to more stable oils, to oils having higher concentrations of antioxidants, to oils having more effective antioxidants, or to oils having more stable base stocks.

The use of HPDSC as described herein provides a measure of stability through oxidative induction times. An ester base stock can be blended with a constant amount of dioctyl diphenylamine which is an antioxidant. This fixed amount of antioxidant provides a constant level of protection for any ester base stock against bulk oxidation. Thus, 0118 tested in this manner with longer induction times have greater intrinsic resistance to oxidation.

The present inventors have developed a unique ester composition and method for preparing these esters such that they have enhanced thermal/oxidative stability, higher volume resistivity, low metals, low ash and low total acid number, when compared to many conventional ester compositions.

The thermal and oxidative stability which is designed into the novel ester compositions of the present invention can permit the formulation to eliminate or reduce the level of antioxidant which must be added to a particular lubricant, thereby providing a substantial cost savings to lubricant manufacturers.

Additionally, the synthetic polyol ester base stocks according to the present invention incorporate a lesser amount of straight-chain and branched-chain monocarboxylic acids having five and six carbon atoms than conventional polyol esters used in the formulation of aircraft turbine oils, thereby markedly reducing the odor. While normal $C_5$ acids and branched $C_5$ acids including trimethylacetic acid are judged to provide thermal/oxidative stability, they are a marketing issue in that $C_5$ acids are highly malodorous and any time there is saponification of the polyol ester and free $C_5$ acid is generated, customers are acutely aware of its presence. Thus, it would be highly desirable to formulate a polyol ester base stock for use in aircraft turbine oils which has reduced amounts of $C_5$ and $C_6$ acids, while exhibiting satisfactory thermal and oxidative stability and still meeting the requirements of Military Specification MIL-L-23699C or MIL-L-23699D.

The chemical and physical requirements for Military Specification MIL-L-23699C and 23699D are set forth below in Table 1.

TABLE 1

(MIL-L-23699C)

| Requirement | Limits | | | Test Method |
|---|---|---|---|---|
| Viscosity @ −40° C. (−40° F.) | 13,000 cSt | | | ASTM D 2532 |
| Viscosity % change after 72 hr @ −40° C. (−40° F.) | ±6 cSt | | | ASTM D 2532 |
| Viscosity @ 98.9° C. (210° F.) | 5.0–5.5 cSt | | | ASTM D 445 |
| Viscosity @ 37.8° C. (100° F.) | 25.0 cSt | | | ASTM D 445 |
| Flash point, minimum | 246° C. (475° F.) | | | ASTM D 92 |
| Pour point, maximum | −54° C. (−65° F.) | | | ASTM D 97 |
| Total Acid Number (TAN), maximum | 0.5 | | | ASTM D 664 |
| Thermal stability and corrosivity @ 274° C. (525° F.) | | | | 3411 of FED-STD-791 |
| Viscosity change, % maximum | 5.0 | | | |
| Total acid number change, maximum | 6.0 | | | |
| Weight of metal change, maximum | 4.0 mg/cm$^2$ | | | |
| Corrosion and Oxidation stability | | | | 5308 of FED-STD-791 |
| after 72 hours at test temperature | 175° C. | 204° C. | 218° C. | |
| Viscosity % change | −5 to 15 | −5 to 25 | | |
| Total acid number, change maximum | 2.0 | 3.0 | | |
| Metal weight change mg/cm$^2$ | | | | |
| steel | ±0.2 | ±0.2 | ±0.2 | |
| silver (Ag) | ±0.2 | ±0.2 | ±0.2 | |
| aluminum (Al) | ±0.2 | ±0.2 | ±0.2 | |
| magnesium (Mg) | ±0.2 | ±0.2 | — | |
| copper (Cu) | ±0.4 | ±0.4 | — | |
| titanium (Ti) | — | — | ±0.2 | |

Generally, polyol esters used in forming aircraft turbine oils typically include a mixture of monopentaerythritol and dipentaerythritol esters. Still others have blended trimethylolpropane esters and dipentaerythritol esters, trimethylolpropane esters and monopentaerythritol/dipentaerythritol esters, or a mixture of trimethylolpropane esters and monopentaerythritol esters.

For example, U.S. Pat. No. 4,826,633 (Carr et al.), which issued on May 2, 1989, is directed to a synthetic ester base stock for use in lubricants for gas turbine engines which meet the specifications of the bearing rig test referred to in military specification ML-23699C. The synthetic ester base stock disclosed in Carr et al. is formed by reacting at least one of monopentaerythritol and trimethylolpropane with a mixture of aliphatic monocarboxylic acids, The mixture of acids includes straight-chain acids having from 5 to 10 carbon atoms and an iso-acid having from 6 to 10 carbon atoms, preferably iso-nonanoic acid. This synthetic ester base stock when mixed with a standard lubricant additive package provides a lubricant having a viscosity at 210° F. (99° C.) of at least about 5.0 centistokes and a pour point of at least as low as about −65° F. (−54° C.). Carr et al. teaches away from the use of technical grade pentaerythritol which includes 11–13 wt. % dipentaerythritol. Carr et al. argues that the dipentaerythritol contained in technical grade pentaerythritol produces an ester lubricant which exhibits increased carbonization and depositing along the oil-air-metal interface compared to that of esters formed without dipentaerythritol. Moreover, Carr et al. neither described nor suggested how much $C_5$ acids can be used in forming the ester base stock to avoid the odor generated from the release of valeric acid and still satisfy the military specifications discussed above.

U.S. Pat. No. 4,124,513 (Yaffe) and U.S. Pat. No. 4,141,845 (Yaffe) both relate to synthetic lubricating oil compositions having improved oxidation stability. The ester base oil used to prepare the lubricant according to either Yaffe patent consists of: technical grade pentaerythritol ester made from a mixture of carboxylic acid consisting of: iso-$C_5$, normal $C_5$, normal $C_6$, normal $C_7$, normal $C_8$ and normal $C_9$. Therefore, the Yaffe patents disclose that up to 51 mole % of $C_5$ and $C_6$ acids is the preferred base stock which teaches away from that recited in this invention.

Co-pending U.S. patent application, Ser. No. 08/284,777 (Ashcraft et al.), which was filed on Aug. 2, 1994, is directed to a synthetic ester base stock for use in formulating aircraft turbine oil which comprises the reaction product of: (a) technical pentaerythritol, and (b) a mixture of $C_5$–$C_{10}$ carboxylic acids. The mixture of $C_5$–$C_{10}$ carboxylic acids comprises: (1) from 5 to 20 mole % of at least one $C_8$–$C_{10}$ carboxylic acid each having 6 or less reactive hydrogens, (2) from 50 to 65 mole % of at least one $C_5$–$C_7$ carboxylic acid each having 6 or less reactive hydrogens, and (3) at least 15 mole % of at least one $C_6$–$C_{10}$ carboxylic acid each having more than 6 reactive hydrogens. The $C_5$–$C_7$ carboxylic acid is preferably n-pentanoic acid or 2-methylbutanoic acid. This teaches away from the ester base stock according to the present invention which requires that the amount of $C_5$ acid is substantially reduced to avoid the release of malodorous $C_5$ acid.

Every lubricant has a characteristic odor which is imparted to it by the compositional changes which occur when used in an engine. In particular, if there is any decomposition of the ester component, it is expected that free carboxylic acid will be generated. In general, hydrolysis of synthetic ester base stocks containing significant amounts of lower molecular weight acid give rise to decomposition products of greater odor intensity than those containing lesser amounts of lower molecular weight acids. By lower molecular weight acids the present inventors mean pentanoic and, to a lesser extent, hexanoic acids which have five or six carbon atoms, respectively. Further, both straight-chain and branched-chain acids are included in this definition. This is true whether the lower molecular weight acids are combined with trimethylolpropane, monopentaerythritol or dipentaerythritol.

It is an object of the present invention to make a high stability synthetic lubricant base stock which provides lubricants having viscosity and pour point characteristics capable of meeting the military specifications for aircraft turbine oils, while minimizing the amount of pentanoic and hexanoic acids contained therein.

The present inventors have developed a unique synthetic ester base stock for use in aircraft turbine oil lubricants having a decreased tendency to release malodorous pentanoic and hexanoic acids when used in an aircraft turbine engine. Furthermore, the synthetic ester base stock of the present invention when combined with a standard lubricant additive package provides a lubricant which meets military specification MIL-L-23699C or MIL-L-23699D with a viscosity at 210° F. (99° C.) of at least 5.0 cSt and at -40° C. of no more than 13,000 cSt, and a pour point of less than at least -65° F. (-54° C.). This ester base stock also exhibits excellent thermal and oxidative stability characteristics.

The present invention also provides many additional advantages which shall become apparent as described below.

SUMMARY OF THE INVENTION

A synthetic ester composition exhibiting thermal and oxidative stability which comprises the reaction product of: (a) a polyol which comprises at least dipentaerythritol, e.g., a polyol selected from the group of technical grade pentaerythritol and a mixture of technical grade pentaerythritol or dipentaerythritol and monopentaerythritol; and (b) a mixture of monocarboxylic acids comprising at least one linear acid selected from the group consisting of between $C_5$–$C_{10}$ acids and at least one branched acid selected from the group consisting of $C_7$–$C_9$ acids, wherein the amount of $C_5$ and $C_6$ acids is between about 20 to 45 weight %, based upon the total amount of monocarboxylic acids, and wherein said synthetic ester composition has a viscosity of at least 4 cSt at 99° C., a viscosity of less than about 11,000 cSt at -40° C. (more preferably less than about 8,000 cSt), and a pour point of at least as low as -54° C.

The preferred synthetic ester compositions according to the present invention have a low metals (i.e., approximately 10 ppm or less metals based on the total ester product, preferably 2 ppm or less), low ash (i.e., approximately 15 ppm or less ash based on the total ester product, preferably 3 ppm or less), and low total acid number (TAN) (i.e., approximately 0.05 mg KOH/g or less for simple esters).

The resultant synthetic ester composition according to the present invention exhibits a thermal/oxidative stability measured by HPDSC isothermal at 220° C., 3.445 MPa air and 0.5 wt. % Vanlube® 81 antioxidant (i.e., dioctyl diphenyl amine) of greater than 20 minutes, preferably greater than 25 minutes.

The present invention also includes a lubricant which is prepared from at least one synthetic ester composition exhibiting thermal and oxidative stability which comprises the reaction product of: (a) a polyol selected from the group consisting of technical grade pentaerythritol and a mixture of technical grade pentaerythritol and monopentaerythritol; and (b) a mixture of monocarboxylic acids comprising at least one linear acid selected from the group consisting of between $C_5$–$C_{10}$ acids and at least one branched acid selected from the group consisting of $C_7$–$C_9$ acids, wherein the amount of $C_5$ and $C_6$ acids is between about 20 to 45 weight %, based upon the total amount of the mixture of monocarboxylic acids, and wherein the synthetic ester composition has a viscosity of at least 4 cSt at 99° C., a viscosity of less than about 11,000 cSt at -40° C. (preferably less than about 8,000 cSt), &viscosity index of at least 120 and a pour point of at least as low as -54° C.; and a lubricant additive package.

The lubricant is preferably an aircraft turbine oil and any other lubricant application which requires high thermal and oxidative stability, reduced odor, higher viscosities and lower pour points.

The additive package comprises at least one additive selected from the group consisting of: viscosity index improvers, corrosion inhibitors, antioxidants, dispersants, lube oil flow improvers, detergents and rust inhibitors, pour point depressants, anti-foaming agents, anti-wear agents, seal swellants, friction modifiers, extreme pressure agents, color stabilizers, demulsifiers, wetting agents, water loss improving agents, bactericides, drill bit lubricants, thickeners or gellants, anti-emulsifying agents, metal deactivators, and additive solubilizers.

Still other lubricants can be formed according to the present invention by blending this unique synthetic ester composition and at least one additional base stock selected from the group consisting of: mineral oils, highly refined mineral oils, poly alpha olefins, polyalkylene glycols, phosphate esters, silicone oils, diesters, polyisobutylenes and polyol esters.

The present invention also involves a process for preparing a synthetic ester composition which comprises the steps of reacting (a) a polyol selected from the group consisting of technical grade pentaerythritol and a mixture of technical grade pentaerythritol and monopentaerythritol; and (b) a mixture of monocarboxylic acids comprising at least one linear acid selected from the group consisting of between $C_5$–$C_{10}$ acids and at least one branched acid selected from the group consisting of $C_7$–$C_9$ acids, wherein the amount of $C_5$ and $C_6$ acids is between about 20 to 45 weight %, based upon the total amount of said mixture of monocarboxylic acids, with or without an esterification catalyst, at a temperature in the range between about 140 to 250° C. and a pressure in the range between about 30 mm Hg to 760 mm Hg (3.999 to 101.308 kPa) for about 0.1 to 12 hours, preferably 0.25 to 8 hours, most preferably 0.25 to 6 hours. This step is preferably followed by removal of any excess carboxylic acid and then followed by the addition of adsorbents to the ester product, thereby allowing the formation of an ester product having low metals, low ash, low total acid and high volume resistivity.

DESCRIPTION OF THE PREFERRED EMBODIMENTS

An improved aircraft turbine oil lubricant can be prepared by reacting technical grade pentaerythritol or a mixture of technical grade pentaerythritol and monopentaerythritol with a mixture of monocarboxylic acids, including a $C_5$–$C_{10}$ linear alkanoic acid, and 2-methylhexanoic, 2-ethylpentanoic and 3,5,5-trimethylhexanoic acid as the preferred branched acids. The linear acids include those having between 5 to 10 carbon atoms, such as valeric acid (pentanoic acid), caproic acid (hexanoic acid), oenanthic acid (heptanoic acid), caprylic acid (octanoic acid), pelargonic acid (nonanoic acid), and caparic acid (decanoic acid).

The ester base stock according to the present invention has a decreased tendency to form malodorous pentanoic and hexanoic acids when used in a gas turbine engine (e.g., an aircraft turbine engine) as compared with other commercial aircraft turbine oil base stocks containing in excess of 50 mole % pentanoic acid.

An esterification process used to make esters comprises the reaction (a) a polyol selected from the group consisting of technical grade pentaerythritol and a mixture of technical grade pentaerythritol and monopentaerythritol; and (b) a mixture of monocarboxylic acids comprising at least one linear acid selected from the group consisting of between $C_5$–$C_{10}$ acids and at least one branched acid selected from the group consisting of $C_7$–$C_9$ acids, wherein the amount of $C_5$ and $C_6$ acids is between about 20 to 45 weight %, based upon the total amount of the mixture of monocarboxylic acids. The synthetic ester base stock of the present invention when admixed with a lubricant additive package provides a lubricant system meeting the MIL-L-23699C or MIL-L-23699D specifications including having a viscosity at 210° F. (99° C.) of at least 5.0 cSt, a viscosity at −40° C. of less than 13,000, and a pour point of at least as low as about −65° F. (−54° C.). The resulting synthetic ester composition preferably exhibits the following properties: a metals content of 10 ppm or less metals based on the total synthetic ester composition, an ash content of 15 ppm or less ash based on the total synthetic ester composition, and a total acid number of 0.05 mg KOH/g or less.

The preferred esterification process includes the following steps:

(a) esterification of a polyol or polyol mixture with excess acid mixture, with or without a sulfuric acid, phosphorus acid, sulfonic acid, para-toluene sulfonic acid or titanium, zirconium or tin-based catalyst at a temperature in the range between about 140 to 250° C. and a pressure in the range between about 30 mm Hg to 760 mm Hg (3.999 to 101.308 kPa) for about 0.1 to 12 hours, preferably 0.25 to 8 hours, most preferably 2 to 8 hours. The stoichiometry in the reactor is variable, with the capability of vacuum stripping excess acids to generate the preferred final composition;

(b) addition of adsorbents such as alumina, silica gel, zeolites, activated carbon, clay and/or filter aid to the reaction mixture following esterification before further treatment, but in certain cases clay treatment may occur later in the process following either flash drying or steam or nitrogen stripping;

(c) addition of water and base to simultaneously neutralize the residual organic and mineral acids and/or hydrolyze the catalyst and, optionally, addition of activated carbon during hydrolysis;

(d) removal of the water used in the hydrolysis step by heat and vacuum in a flash step;

(e) filtration of solids from the ester mixture containing the bulk of the excess acids used in the esterification reaction;

(f) removal of excess acids by steam stripping or any other distillation method and recycling of the alcohol to the reaction vessel; and (g) removing any residual solids from the stripped ester in a final filtration.

The addition of adsorbents such as alumina, silica gel, zeolites, activated carbon, clay and/or filter aid to the reaction mixture following esterification as described in step (b) above, allows for the formation of an ester product having low metals (i.e., approximately 10 ppm or less metals based on the total ester product), low ash (i.e., approximately 15 ppm or less ash based on the total ester product), and low total acid number (TAN) (i.e., approximately 0.05 mg KOH(g or less for simple esters and less than 2 for complex esters).

When it is desirable to use esterification catalysts, titanium, zirconium and tin-based catalysts such as titanium, zirconium and tin alcoholates, carboxylates and chelates are preferred. See U.S. Pat. No. 3,056,818 (Werber) and U.S. Pat. No. 5,324,853 (Jones et al.) which disclose various specific catalysts which may be used in the esterification process of the present invention and which are incorporated herein by reference. It is also possible to use sulfuric acid, phosphorus acid, sulfonic acid and para-toluene sulfonic acid as the esterification catalyst, although they are not as preferred as the metal catalysts discussed immediately above.

ACIDS

Monocarboxylic acids which undergo esterification can be selected from the group consisting of: $C_5$–$C_{10}$ linear acids and $C_5$–$C_{10}$ branched acids, more preferably $C_7$–$C_9$ branched acids. Suitable linear acids include, but are not limited to, valeric acid, oenanthic acid, caprylic acid, pelargonic acid and capric acid. The branched acids may be iso-$C_5$, iso-$C_7$, iso-$C_8$ or iso-$C_9$. Preferably, the branched acids used are an iso-$C_7$ acid, and the iso-$C_9$ acid (e.g., 3,5,5-trimethylhexanoic acid). As used herein, iso-$C_7$ acid is about 60–90 wt. % 2-methylhexanoic acid and about 10–40 wt. % 2-ethylpentanoic acid. Another preferred branched acid is 3,5,5-trimethylhexanoic acid derived from the oxonation/oxidation of diisobutlylene. The preferred branched acid is a mixture of an iso-$C_7$ which is present in an amount of about 60 to 100 weight % and an iso-$C_9$ (i.e.; 3,5,5-trimethylhexanoic acid) which is, present in an amount of about 0 to 40 weight percent of the total iso-acid component. The linear acid component preferably include an amount of heptanoic acid equal to about 1.5 to 3.5 times the amount of iso-heptanoic acid.

One preferred acid mixture comprises heptanoic acid, valeric acid, iso-heptanoic acid, and 3,5,5-trimethylhexanoic acid. Another preferred acid mixture comprises heptanoic acid, valeric acid, iso-heptanoic acid, isooctanoic acid, and 3,5,5-trimethylhexanoic acid. It is most preferable that the linear acid component be present in the total acid mixture in an amount between about 50 to 95 weight %, more preferably 60 to 85 weight %, with the remainder being mono-carboxylic branched acids, preferably iso-heptanoic acid and iso-nonanoic.

If the iso-acid is iso-heptanoic then it is preferable that it be a mixture of acids comprising 60 to 80 weight % of 2-methylhexanoic acid, 0 to 10 weight % heptanoic acid and 10 to 40 weight % 2-ethylpentanoic acid.

The acid composition as herein described provides the necessary viscosity characteristics and with the preferred formulations minimizes the odor forming lower molecular weight acids ($C_5$ and $C_6$).

Branching on the acids is acceptable with the right acids. This means that one has to balance the kind and amount of branching to best meet the performance requirements. In terms of low temperature viscosity, the less branching the better. Set forth below are various $C_9$ esters and their respective do stabilities as measured by HPDSC:

| Ester | Stability as Measured by HPDSC (minutes) |
|---|---|
| 3,5,5-trimethylhexanoic acid | 118.0 |
| n-$C_9$ | 14.2 |

POLYOLS

The preferred polyol used in accordance with the present invention is technical grade pentaerythritol which comprises about 88% mono-pentaerythritol, 10% di-pentaerythritol and 1-2% tri-pentaerythritol. Alternatively, the polyol can be a mixture of technical grade pentaerythritol and monopentaerythritol, wherein the technical grade pentaerythritol is present in an amount between about 50 to 95 weight percent, preferably 80 to 95 weight percent, of the polyol and the mono-pentaerythritol is present in an amount between about 5 to 50 weight percent, preferably 5 to 20 weight percent, of the total polyol.

The acid mixture is present in the reaction to form the ester in an excess of about 10 to 20 mole % for the amount of polyol used. The excess acid is used to force the reaction to completion. The composition of the feed acid is adjusted so as to provide the desired composition of product ester. After the reaction is complete, the excess acid is removed by stripping and refining.

The ester composition according to the present invention can either be used by itself as a lubricant base stock or in admixture with other base stocks, such as mineral oils, highly refined mineral oils, poly alpha olefins (PAO), polyalkylene glycols (PAG), phosphate esters, silicone oils, diesters, polyisobutylenes and polyol esters.

The ester composition according to the present invention can be used in the formulation of various lubricants such as, aircraft and other turbine oils. The preferred lubricant is prepared from at least one synthetic ester composition formed according to the present invention and a lubricant additive package.

Lubricants prepared in accordance with the present invention have a decreased tendency to form odors arising from high concentrations of low molecular weight acids (e.g., $C_5$ and $C_6$ acids) when used in aircraft turbine engines. By providing a mixture of synthetic esters prepared with significant amounts of a mono-branched acids, and relatively small amounts of di-branched, tri-branched and higher branched acids in accordance with the present invention, synthetic ester lubricants with improved low temperature viscosity and a synthetic ester lubricants with improved odor characteristics when used in an aircraft turbine engine are obtained. The ester mixture is prepared by esterifying either pure technical grade pentaerythritol or a mixture of technical grade pentaerythritol and mono-pentaerythritol with an acid mixture of normal $C_5$–$C_{10}$ carboxylic acids provided that the combined amount of $C_5$ and $C_6$ acids is less than 45%, based on the total acid content, and a mono-branched iso-acid, preferably iso-heptanoic acid (i.e., a mixture of 2-methylhexanoic acid with a minor amount of 2-ethylpentanoic acid); thereby reducing the odor forming tendency of the ester. The mixture of esters prepared in accordance with this invention are compatible with conventional lubricant additives which are typically added to the polyol ester base stock to improve the properties of the synthetic ester mixtures.

AIRCRAFT TURBINE OILS

The ester composition or blends thereof can be used in the formulation of aircraft turbine oils together with selected lubricant additives. The preferred aircraft turbine oil is typically formulated using the ester composition formed according to the present invention together with any conventional turbine oil additive package. The additives listed below are typically used in such amounts so as to provide their normal attendant functions. The additive package may include, but is not limited to, viscosity index improvers, corrosion inhibitors, antioxidants, thickeners, dispersants, anti-emulsifying agents, color stabilizers, detergents and rust inhibitors, and pour point depressants.

The aircraft turbine oil according to the present invention can employ typically about 95 to 99.99% base stock, with the remainder comprising an additive package, typically in the range between about 0.01 to about 5.0 weight percent each, based on the total weight of the composition.

Additional additive packages for use in forming aircraft turbine oils according to the present invention are set forth in U.S. Pat. No. 4,124,513 (Yaffe), which issued on Nov. 7, 1978, and U.S. Pat. No. 4,141,845 (Yaffe), which issued on Feb. 27, 1979, both of which are incorporated herein by reference. One, preferred adpack includes an alkylphenyl or alkarylphenyl naphthylamine, a dialkyldiphenylamine, a polyhydroxy anthraquinone, a hydrocarbyl phosphate ester and an S-alkyl-2-mercaptobenzothiazole. Another preferred adpack includes an alkylphenyl or alkarylphenyl naphthylamine, a dialkyldiphenylamine, a polyhydroxy anthraquinone, a hydrocarbyl phosphate ester and an N-alkyl-benzothiazole-2-thione.

It is extremely important in many lubricant applications such as aircraft turbine oils to provide a lubricant product which is thermally and oxidatively stable. One means of measuring relative thermal and oxidative stability in lubricants is via high pressure differential scanning calorimetry (HPDSC). In the tests set forth hereafter, the samples are heated to a fixed temperature and held there under a pressure of air (or oxygen) and the time to onset of decomposition is measured. The longer the time to decomposition, the more stable the sample.

EXAMPLE 1

A variety of ester base stocks were prepared. In each of the following runs the raw materials identified in Table 2 below were charged to a stirred reactor capable of delivering up to about 470° F. (243.3° C.) and a vacuum of at least 60 mm of mercury. The reactor was provided with a nitrogen sparge and a stirrer. The charge was heated to a reaction temperature between about 420–460° F. (215.5–237.8° C.) and the water of reaction was collected in a trap while the acids were returned to the reactor. Vacuum was applied as required in order to maintain a reasonable reflux rate. At the end of the reaction, the excess acid was removed either by vacuum stripping or by vacuum stripping in combination with treatment with soda ash and water. The resulting ester base stock was dried and filtered. The viscosities at 100° C., 40° C., and −40° C. were determined in accordance with ASTM D-445 for each sample base stock together with the pour point in accordance with ASTM D-97. The viscosity index (VI) was calculated from the viscosity data at 100° C. and 40° C.

TABLE 2

| Sample | Acids | Alcohol | Vis. −40° C. cSt | Vis. 100° C. cSt | VI | Compat- w/PVC @ 50 hr |
|---|---|---|---|---|---|---|
| A | n-$C_5$, n-$C_7$, $C_{8-10}$, and i-$C_9$ (30/40/20/10 wt. %) | Tech. PE* | 12,485 | 5.49 | 145 | — |
| B | n-$C_5$, n-$C_7$, and $C_{8-10}$ (30/35/15/20 wt. %) | Tech. PE* | 9,710 | 5.17 | 140 | — |
| C | n-$C_5$, i-$C_5$, n-$C_7$, i-$C_7$, and $C_{8-10}$ (21/9/35/15/20 wt. %) | Tech. PE* | 14,495 | 5.69 | 132 | No |
| D | n-$C_5$, n-$C_7$, and i-$C_7$ (25/60/15 wt. %) | Tech. PE* | 10,299 | 4.96 | 133 | Yes |
| E | n-$C_7$ and $C_{8-10}$ (85/15 wt. %) | Mono PE** | solid | 4.93 | 148 | No |
| F | n-$C_5$, n-$C_7$, i-$C_7$, and i-$C_9$ (38/32/22/8 wt. %) | Tech. PE* | 7,513 | 4.83 | 124 | Yes |

*Tech. PE is technical grade pentaerythritol which comprises 88% mono-pentaerythritol, 10% di-pentaerythritol and 1-2% tri-pentaerythritol.
**Mono PE is monopentaerythritol.

Sample F is an ester base stock formed in accordance with the present invention. It is the only ester base stock listed in Table 2 which has a viscosity at −40° C. of less than 8,000 cSt such that the formulated aircraft turbine oil will exhibit a viscosity at −40° C. of less than 13,000 cSt such that it meets Military Specification MIL-L-23699C or D, while also exhibiting a decreased tendency to form malodorous pentanoic acid when used in an aircraft turbine engine since its $C_5$ level is below 50 wt. %.

EXAMPLE 2

Table 3 below compares the total amount of $C_5$ acids in two conventional aircraft turbine oils versus the amount of $C_5$ acids in an aircraft turbine oil formulation which incorporates the base stock formed in accordance with the present invention.

TABLE 3

| Lubricant | % iso-$C_5$ acids | % n-$C_5$ acids | Total $C_5$ acids |
|---|---|---|---|
| Mobil Jet 2 | 18.0 | 37.0 | 55.0 |
| Mobil 254 | 10.5 | 41.0 | 51.5 |
| Reduced Odor Ester* | 38.0 | 0 | 38.0 |

*Denotes an aircraft turbine oil prepared from the reaction product of technical grade pentaerythritol, 38% n-$C_5$ acid, 32% n-$C_7$, 22% iso-$C_7$, and 8% 3,5,5-trimethylhexanoic acid and an additive package comprising: amine antioxidants, antiwear additives, etc.

The reduced odor aircraft turbine oil formulation of the present invention which is set forth above in Table 3 has a total $C_5$ and $C_6$ acid content that is substantially below either Mobil Jet 2 or Mobil 254, thus having a concomitant reduction in seal swell and in odor potential. Furthermore, the viscosity at 100° C. of all of the above formulations is less than the 13,000 ceiling set in Military Specification MIL-L-23699C or D.

EXAMPLE 3

Stability is one of the most important criteria for aircraft turbine oil esters. Table 4 below lists some esters, including the ester of the present invention, and their HPDSC measured stabilities, along with viscosity information. All stability data was taken at 220° C., 500 psi (3.445.MPa) air, and 0.5% V-81 antioxidant.

TABLE 4

| Ester | | HPDSC | Viscosity (cSt) | |
|---|---|---|---|---|
| Alcohol | Acids | (minutes) | 40° C. | 100° C. |
| TPE* | 46% $C_5$/48% 1770**/5% iso-$C_9$ | 46.7 | 23.9 | 4.60 |
| TPE* | 25% $C_5$/50% iso-$C_7$/25% n-$C_7$ | — | 25.8 | 5.02 |
| TPE* | 30% n-$C_5$/50% iso-$C_7$/20% n-$C_{810}$*** | — | 26.4 | 5.17 |
| MonoPE**** | 25% n-$C_5$/75% iso-$C_7$ | — | 21.2 | 4.44 |
| TPE* | 25% $C_5$/50% iso-$C_7$/25% n-$C_7$ | — | 25.3 | 4.96 |
| TPE* | 30% $C_5$/50% iso-$C_7$/20% n-$C_7$ | — | 23.2 | 4.72 |
| TMP# | $C_{7810}$ | 23 | 18.0 | 4.0 |
| Hercoflex 707***** | | 28.13 | | |
| TPE/n-$C_9$ | | 16.9 | 31 | 6.0 |
| TEP | 2-Ethylhexanoic acid | 17.5 | 50 | 6.7 |
| TPE | 1770** | 19.23 | 24.4 | 5.0 |

*TPE denotes technical grade pentaerythritol.
TMP denotes trimethylolpropane.
**1770 is a $C_7$ acid made up of ca. 70% n-$C_7$, 25% 2-methylhexanoic acid, and 5% 2-ethylpentanoic acid.
***$C_{810}$ denotes is a mixture of 55% n-$C_8$ and 45% n-$C_{10}$ acids.
****MonoPE is monopentaerythritol.
*****Hercoflex 707 is dipentaerythritol mixed with $C_5$–$C_9$ linear acids.

The ester base stock according to the present invention (i.e., technical grade pentaerythritol with 46% $C_5$, 48% 1770, and 5% iso- $C_9$) exhibited a thermal/oxidative stability as measured by HPDSC of about 46.7 minutes and a viscosity at 100° C. of at least 4 cSt. None of the other comparative examples was able to have both good stability and acceptable viscosity at 100° C.

EXAMPLE 4

An ester base stock according to the present invention was prepared by adding 42.27 kg of n-$C_7$ acid, 30.85 kg of iso-$C_7$ acid, 58.06 kg of n-$C_5$ and 9.98 kg of 3,5,5-trimethylhexanoic acid to a reactor under esterification conditions. The resultant ester product had the following properties set forth in Table 5 below.

TABLE 5

| Physical Property | |
|---|---|
| Molecular Weight | 538 |
| Number of Branches per Molecule | 0.3 |
| Viscosity (cSt) | |
| −40° C. | 7619.00 |
| 40° C. | 23.88 |
| 100° C. | 4.64 |
| Hydroxyl Number (mgKOH/gm) | 4.8 |
| SUM Metals, ppm | 0 |
| Odor from $C_5$ acid | Lower than conventional aircraft turbine synthetic ester base stocks |
| Thermal/Oxidative Stability HPDSC (onset of decomposition under air at 220° C.) | 46.7 minutes |
| Pour Point (° C.) | −80 |
| Total Acid Number | 0.04 |
| Water (ppm) | 149 |
| Viscosity Index (VI) | 122 |
| Flash Point (° C.) | 246.11 |
| Specific Gravity | 0.9966 |
| % Conversion (Gas Chromatography) | 97.9 |

The above synthetic ester base stock has been designed by the present inventors such that it meets or exceeds the physical characteristic requirements of Military Specification No. MIL-L-23699C or D for an aviation turbine oil base stock. The other major advantage of this ester base stock is the reduction in the $C_5$ content which substantially reduces odor of the base stock. Finally, although the ester base stock according to the present invention has lower levels of $C_5$ acids, it has been shown to exhibit higher thermal and oxidative stability than conventional polyol ester base stocks.

We claim:

1. A synthetic ester composition exhibiting thermal and oxidative stability which comprises the reaction product of:
   (a) a polyol which comprises at least dipentaerythritol; and
   (b) a mixture of monocarboxylic acids comprising at least one linear acid selected from the group consisting of between $C_5$–$C_{10}$ acids and at least one branched acid selected from the group consisting of $C_7$–$C_9$ acids, wherein the amount of $C_5$ and $C_6$ acids is between about 20 to 45 weight %, based upon the total amount of said mixture of monocarboxylic acids,
   wherein said synthetic ester composition has a viscosity of at least 4 cSt at 99° C., a viscosity of less than about 11,000 cSt at −40° C., a viscosity index of at least 120, and a pour point of at least as low as −54° C.; and
   wherein said synthetic ester composition exhibits the following properties: a thermal/oxidative stability measured by HPDSC at 220° C., 3.445 MPa air and 0.5 wt. % dioctyl diphenyl amine of at least 25 minutes; a metals content of 10 ppm or less metals based on the total synthetic ester composition; an ash content of 15 ppm or less ash based on the total synthetic ester composition; and a total acid number of 0.05 mg KOH/g or less.

2. The synthetic ester composition according to claim 1 wherein said viscosity at −40° C. is less than about 8,000.

3. The synthetic ester composition according to claim 1 wherein said synthetic ester composition is formed by esterification of said polyol with excess mixture of acids, with or without a sulfonic acid, phosphorus acid, sulfonic acid, para-toluene sulfuric acid or titanium, zirconium or tin-based catalyst, at a temperature in the range between about 140 to 250° C. and a pressure in the range between about 30 mm Hg to 760 mm Hg.

4. The synthetic ester composition according to claim 3 further comprising the step of adding an adsorbent to said reaction mixture: following esterification.

5. The synthetic ester composition according to claim 4 wherein said adsorbent is at least one material selected from the group comprising:
   alumina, silica gel, activated carbon, zeolites, clay and filter aid.

6. The synthetic ester composition according to claim 3 further comprising the steps of:
   addition or water and base to simultaneously neutralize the residual organic and mineral acids and/or hydrolyze said catalyst;
   removal of said water used in the hydrolysis step by heat and vacuum in a flash step;
   filtration of solids from said ester mixture containing the bulk of the excess acids used in the esterification reaction;
   removal of excess acids by steam stripping or any other distillation method; and
   removing any residual solids from the stripped ester in a final filtration.

7. The synthetic ester composition according to claim 1 wherein said linear acids are selected from the group consisting of: valeric acid, hexanoic acid, heptanoic acid, caprylic acid, pelargonic acid and capric acid.

8. The synthetic ester composition according to claim 1 wherein said branched acids are selected from the group consisting of: 2-methylhexanoic, 2-ethylpentanoic, and 3,5,5-trimethylhexanoic acid.

9. The synthetic ester composition according to claim 1 wherein said polyol comprises technical pentaerythritol in an amount between about 50 to 100 weight %, based on the total polyol, and monopentaerythritol in an amount between about 0 to 50 weight %, based on the total polyol.

10. The synthetic ester composition according to claim 1 wherein said branched acid is iso-heptanoic acid present in an amount between about 3 to 50 weight %, based on the total acid.

11. The synthetic ester composition according to claim 10 wherein said linear acid includes heptanoic acid which is present in an amount between about 1.5 to 3.5 times the amount of iso-heptanoic acid.

12. The synthetic ester composition according to claim 1 wherein said amount of $C_5$ and $C_6$ acids is between about 20 to 41.13 weight %, based upon the total amount of said mixture of monocarboxylic acids.

13. The synthetic ester composition according to claim 1 wherein said amount of $C_5$ and $C_6$ acids is between about 20 to 38 weight %, based upon the total amount of said mixture of monocarboxylic acids.

14. A lubricant which is prepared from:
   at least one synthetic ester composition exhibiting thermal and oxidative stability which comprises the reaction product of: (a) a polyol which comprises at least dipentaerythritol; and (b) a mixture of monocarboxylic acids comprising at least one linear acid selected from the group consisting of between $C_5$–$C_{10}$ acids and at least one branched acid selected from the group consisting of $C_7$–$C_9$ acids, wherein the amount of $C_5$ and $C_6$ acids is between about 20 to 45 weight %, based upon the total amount of said mixture of monocarboxylic acids; and wherein said synthetic ester composition exhibits the following properties: a thermal/oxidative stability measured by HPDSC at 220° C. 3.445 MPa air and 0.5 wt. % dioctyl diphenyl amine of at least 25 minutes; a metals content of 10 ppm or less metals based on the total synthetic ester composition; an ash content of 15 ppm or less ash based on the total synthetic ester composition; and a total acid number of 0.05 mg KOH/g or less; and
   a lubricant additive package wherein the lubricant has a viscosity of at least 5 cSt at 99° C., a viscosity of less than about 13,000 cSt at −40° C., and a pour point of at least as low as about −54° C.

15. The lubricant according to claim 14 wherein said synthetic ester composition is formed by esterification of said polyol with excess mixture of acids, with or without a sulfonic acid, phosphorus acid, sulfonic acid, para-toluene sulfuric acid or titanium, zirconium or tin-based catalyst, at a temperature in the range between about 140 to 250° C. and a pressure in the range between about 30 mm Hg to 760 mm Hg.

16. The lubricant according to claim 15 further comprising the step of adding an adsorbent to said reaction mixture following esterification.

17. The lubricant according to claim 16 wherein said adsorbent is at least one material selected from the group comprising: alumina, silica gel, activated carbon, zeolites, clay and filter aid.

18. The lubricant according to claim 15 further comprising the steps of:
   addition of water and base to simultaneously neutralize the residual organic and mineral acids and/or hydrolyze said catalyst;
   removal of said water used in the hydrolysis step by heat and vacuum in a flash step;
   filtration of solids from said ester mixture containing the bulk of the excess acids used in the esterification reaction;
   removal of excess acids by steam stripping or any other distillation method; and
   removing any residual solids from the stripped ester in a final filtration.

19. The lubricant according to claim 14 wherein said linear acids are selected from the group consisting of: valeric acid, hexanoic acid, heptanoic acid, caprylic acid, pelargonic acid and capric acid.

20. The lubricant according to claim 14 wherein said branched acids are selected from the group consisting of: 2-methylhexanoic, 2-ethylpentanoic, and 3,5,5-trimethylhexanoic acid.

21. The lubricant according to claim 14 wherein said polyol comprises technical pentaerythritol in an amount between about 50 to 100 weight %, based on the total polyol, and monopentaerythritol in an amount between about 0 to 50 weight %, based on the total polyol.

22. The lubricant according to claim 14 wherein said branched acid is iso-heptanoic acid present in an amount between about 3 to 50 weight %, based on the total acid.

23. The lubricant according to claim 22 wherein said linear acid includes heptanoic acid which is present in an amount between about 1.5 to 3.5 times the amount of iso-heptanoic acid.

24. The lubricant according to claim 14 wherein said lubricant is a blend of said synthetic ester composition and at least one additional base stock selected from the group consisting of: mineral oils, highly refined mineral oils, poly alpha olefins, polyalkylene glycols, phosphate ester, silicone oils, diesters and polyol ester.

25. The lubricant according to claim 14 wherein said additive package comprises at least one additive selected from the group consisting of: viscosity index improvers, corrosion inhibitors, antioxidants, dispersants, lube oil flow improvers, detergents and rust inhibitors, pour point depressants, anti-foaming agents, anti-wear agents, seal swellants, friction modifiers, extreme pressure agents, color stabilizers, demulsifiers, wetting agents, water loss improving agents, bactericides, drill bit lubricants, thickeners or gellants, anti-emulsifying agents, metal deactivators, coupling agents, surfactants, and additive solubilizers.

26. An aircraft turbine oil formulation which is prepared from:

at least one synthetic ester composition exhibiting thermal and oxidative stability which comprises the reaction product of: (a) a polyol which comprises at least dipentaerythritol; and (b) a mixture of monocarboxylic acids comprising at least one linear acid selected from the group consisting of between $C_5$–$C_{10}$ acids and at least one branched acid selected from the group consisting of $C_7$–$C_9$ acids, wherein the amount of $C_5$ and $C_6$ acids is between about 20 to 45 weight %, based upon the total amount of said mixture of monocarboxylic acids; and wherein said synthetic ester composition exhibits the following properties: a thermal/oxidative stability measured by HPDSC at 220° C., 3.445 MPa air and 0.5 wt. % dioctyl diphenyl amine of at least 25 minutes, a metals content of 10 ppm or less metals based on the total synthetic ester composition; an ash content of 15 ppm or less ash based on the total synthetic ester composition; and a total acid number of 0.05 mg KOH/g or less; and a lubricant additive package, wherein said aircraft turbine oil formulation has a viscosity of at least 5 cSt at 99° C., a viscosity of less than about 13,000 cSt at −40° C., and a pour point of at least as low as −54° C.

27. The formulation according to claim 26 wherein said additive package comprises at least one additive selected from the group consisting of: viscosity index improvers, corrosion inhibitors, antioxidants, dispersants, anti-emulsifying agents, color stabilizers, detergents and rust inhibitors, and pour point depressants.

28. The formulation according to claim 26 wherein said additive package comprises at least one additive selected from the group consisting of: an alkylphenyl or alkarylphenyl naphthylamine, a dialkyldiphenylamine, a polyhydroxy anthraquinone, a hydrocarbyl phosphate ester and an S-alkyl-2-mercaptobenzothiazole.

29. The formulation according to claim 26 wherein said additive package comprises at least one additive selected from the group consisting of an alkylphenyl or alkarylphenyl naphthylamine, a dialkyldiphenylamine, a polyhydroxy anthraquinone, a hydrocarbyl phosphate ester and an N-alkyl-benzothiazole-2-thione.

30. The formulation according to claim 26 further comprising a blend of said synthetic ester composition and at least one additional base stock selected from the group consisting of: mineral oils, highly refined mineral oils, poly alpha olefins, polyalkylene glycols, phosphate ester, silicone oils, diesters and polyol ester.

* * * * *